United States Patent
Saito et al.

(10) Patent No.: US 6,344,209 B1
(45) Date of Patent: Feb. 5, 2002

(54) APATITE-COATED SOLID COMPOSITION

(75) Inventors: Kazuhiro Saito, Suita; Tetsuo Hoshino, Osaka, both of (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 09/403,414

(22) PCT Filed: Apr. 23, 1998

(86) PCT No.: PCT/JP98/01870

§ 371 Date: Oct. 20, 1999

§ 102(e) Date: Oct. 20, 1999

(87) PCT Pub. No.: WO98/47485

PCT Pub. Date: Oct. 29, 1998

(30) Foreign Application Priority Data

Apr. 24, 1997 (JP) ............................................. 9-106918

(51) Int. Cl.[7] .............................. A61F 2/00; A61K 9/52; A61K 9/58; A61K 9/14; A61K 47/30

(52) U.S. Cl. ..................... 424/426; 424/457; 424/462; 424/486; 424/489; 424/490; 424/463; 514/772.3; 514/963

(58) Field of Search .............................. 424/426, 501, 424/457, 462, 463, 486, 489; 514/963, 772.3

(56) References Cited

U.S. PATENT DOCUMENTS

| | | | | |
|---|---|---|---|---|
| 4,623,553 A | * | 11/1986 | Ries et al. | 427/2 |
| 5,071,841 A | | 12/1991 | Sohda et al. | 514/96 |
| 5,158,943 A | | 10/1992 | Sohda et al. | 514/96 |
| 5,290,494 A | * | 3/1994 | Coombes et al. | 264/41 |
| 5,916,597 A | * | 6/1999 | Lee et al. | 424/501 |

FOREIGN PATENT DOCUMENTS

| | | |
|---|---|---|
| DE | 2717506 | 5/1978 |
| EP | 0376197 A | 7/1990 |
| EP | 0389713 A | 10/1990 |
| EP | 0714666 A | 6/1996 |
| JP | 03 232880 A | 10/1991 |
| WO | 9639202 | * 12/1996 |
| WO | WO 97/07788 | 3/1997 |

* cited by examiner

Primary Examiner—Thurman K. Page
Assistant Examiner—Blessing Fubara
(74) Attorney, Agent, or Firm—Mark Chao; Elaine M. Ramesh

(57) ABSTRACT

An apatite-coated solid composition which contains a biodegradable polymer and an apatite-coated solid composition which contains a biodegradable polymer and a medicinal substance have properties of sustained release and of osteoconductive activity.

15 Claims, 4 Drawing Sheets

(1)　　　　　　　　(2)　　　　　　　　(3)

… … …

APATITE-COATED SOLID COMPOSITION

This application is the National Stage of International Application No. PCT/JP98/01870, filed Apr. 23, 1998.

TECHNICAL FIELD

The present invention provides an apatite-coated solid composition containing a biodegradable polymer, an apatite-coated solid composition containing a biodegradable polymer and a medicinal substance, and a method for producing the solid composition.

BACKGROUND ART

The bone and teeth of vertebrates are composed of 70% of a mineral phase and 30% of an organic matrix, with the constitution of the mineral phase closely resembling that of hydroxyapatite. Therefore, investigations into the possible utilization of apatite as a biological material began around 1970. As substitutes for bone, metallic materials such as stainless steel, cobalt-chromium alloy, titanium alloys, etc. and organic compounds such as high density polyethylene, polymethyl methacrylate, etc. had been used for some time. However, since those materials are incapable of being fused directly to the bone tissue, loosening and breakage of the implants occur with a high incidence, inducing adverse responses such as chronic inflammation of the surrounding tissue. To secure a firmer fusion to bone, a technology comprising coating the surface of such a material with hydroxyapatite by, for example, sputtering or plasma spray coating has been developed and is in practice.

Various contrivances were made for securing a firm fusion of biochemical materials to bone, and it was discovered that when $SiO_2$—$Na_2O$—$CaO$—$P_2O_5$ type glass is implanted in bone, an intimate chemical coupling takes place. Further improvements led to the development of an alkali metals-free glass ceramic comprising apatite and wollastonite crystals (the A—W glass ceramic) starting with a powder of $SiO_2$—$CaO$—$P_2O_5$—$MgO$—$CaF_2$ glass via sintering and crystallization. The research into the mechanism of fusion of this material to bone is well-documented and in view of its high mechanical strength, this material has been clinically applied with success as bone graft substitutes for iliac bone and vertebrae.

It was confirmed that between the A—W glass ceramic and bone, there exists a layer of fine poorly oriented apatite crystals formed from the ions released from the A—W glass ceramic and the body fluid components, so that the bone and the implant are intimately bound through this layer. The mechanisms of formation of such an apatite layer have been analyzed using a buffer solution called "simulated body fluid" (SBF) which is free of high molecular components such as proteins and has been prepared to match the body fluid only in the concentrations of ions (Manual of Materials for Orthopaedic Materials, Kanehara & Co., Ltd.). It is reported that by taking advantage of such properties of the A—W glass ceramic, an apatite layer could be formed on an organic polymer such as poly(ethylene terephthalate) by immersing the polymer and A—W glass ceramic together in a simulated body fluid (Journal of Biomedical Materials Research, 29, 349–357, 1995). In connection with this technology, it has been recommended that the surface of the polymer be pretreated by glow discharge.

Regarding the exploitation of biodegradable-absorbable polymers in the development of injectable bone substitutes, it has been reported that in an implantation experiment, new bone formation took place in line with the degradation and absorption of a polylactic acid (PLA)-hydroxyapatite (HA) complex, suggesting the possibility of clinical application of such polymers as bone implants (Collection of Papers on Polymers, 42 (11), 771–776, 1985).

Bone remodelling has been confirmed with an implant material comprising either PLA or poly (DL-lactide-co-glycolide) (PLGA) as a carrier and an osteoinductive factor (bone morphogenetic protein, BMP) or a material comprising a complex of said polymer and hydroxyapatite as a carrier and BMP (Abstract of Lectures at the 24th Medical Polymer Symposium, pages 65–66).

Furthermore, it has been reported that in an experiment involving the implantation of a PLA-polyethylene glycol (PEG) block copolymer-BMP complex or a ternary complex containing hydroxyapatite in addition to the above combination at sites of osseous defect they regenerate bone tissues (Clinical Orthopaedics and Related Research, No. 294, pp. 333–343, 1993), thus suggesting their clinical applicability as bone implants.

Powders containing pharmacologically active substances having an activity of promoting bone formation are useful for the therapy of various diseases of bone (e.g. osteoporosis and bone fracture) by injecting or implanting the powder containing such a pharmacologically active substance. Furthermore, applicability of such powders can be expanded in scope and the effect improved by adding new functions such as sustained release and biodegradability to such powders. Meanwhile, it is known that apatite is composed of calcium phosphate just as is bone, thus having a very high affinity for bone and that, therefore, when administered to a host body, apatite does not induce foreign-body reactions such as immune responses, thus being of great utility. However, pharmacologically active substances and powder materials are generally incapable of withstanding the tortuous conditions of sputtering, plasma spray coating, and other coating operations but undergo degradation in their course.

DISCLOSURE OF INVENTION

The inventors of the present invention thought it possible to effectively exploit the pharmacologic action of a powder containing a drug substance by covering the surface of the powder with apatite and did intensive investigations. As a result, they found that when a powder is immersed in an aqueous solution containing various ions, an apatite coating layer is formed on the surface of the particles with good efficiency under mild conditions. The finding was followed by further research which has culminated in the present invention.

The present invention is:

(1) An apatite-coated solid composition containing a biodegradable polymer, (2) A solid composition according to item (1), which contains a medicinal substance, (3) A solid composition according to item (2), which comprises a sustained release preparation, (4) A solid composition according to item (1), wherein the biodegradable polymer is polylactic acid, polyglycolic acid, or a copolymer of polylactic acid and polyglycolic acid, (5) A solid composition according to item (2), wherein the medicinal substance is hardly soluble in water, (6) A solid composition according to item (2), wherein the medicinal substance is a medicine for prophylaxis or treatment of bone diseases, an antibiotic, an anti-inflammatory agent or an anti-tumor agent, (7) A solid composition according to item (1), wherein the apatite is a crystalline mineral substance which has (1) at least one cation selected from the group consisting of $Na^+$, $K^+$, $H^+$, $Ca^{2+}$, $Sr^{2+}$, $Ba^{2+}$, $Pb^{2+}$, $Zn^{2+}$, $Cd^{2+}$, $Mg^{2+}$, $Fe^{2+}$, $Mn^{2+}$, $Ra^{2+}$, $Al^{3+}$, $Y^{3+}$, $Ce^{3+}$, $Nd^{3+}$, $La^{3+}$ and $Dy^{3+}$, and (2) at least one anion selected from the group consisting of $SO_4^{2-}$, $CO_3^{2-}$, $HPO_4^{2-}$, $PO_3F^{2-}$, $PO_4^{3-}$, $AsO_4^{3-}$, $VO_4^{3-}$, $BO_3^{3-}$, $CrO_4^{3-}$, $SiO_4^{3-}$, $GeO_4^{3-}$, $(CO_3F)^{3-}$ and $BO_4^{5-}$, (8) A solid composition according to item (1), wherein the apatite is hydroxyapatite, (9) A solid composition according to item (1), wherein the apatite is phosphate apatite,

(10) A solid composition according to item (1), which is in a microcapsule preparation,

(11) A solid composition according to item (1), wherein the apatite layer has a honeycomb structure,

(12) A solid composition according to item (1), wherein the apatite layer is about 1 nm to 50 μm,

(13) A method for producing an apatite-coated solid composition containing a biodegradable polymer, which comprises subjecting a substrate of a solid composition containing a biodegradable polymer to immersion in an aqueous ion solution which is capable of forming an apatite,

(14) A method according to item (13), wherein the solid composition contains a medicinal substance,

(15) A method according to item (13), wherein the aqueous ion solution is an aqueous solution which contains at least one of $Na^+$, $K^+$, $Mg^{2+}$, $Ca^{2+}$, $Cl^-$, $CO_3^{2-}$, $PO_4^{3-}$ and $SO_4^{2-}$, and (16) A method according to item (13), wherein the temperature at the immersion is about 10 to 150° C.

The present invention also provides an apatite-coated solid composition containing (1) a biodegradable polymer or (2) a biodegradable polymer and a medicinal substance, which is formed by immersing a substrate of a solid composition containing (1) a biodegradable polymer or (2) a biodegradable polymer and a medicinal substance in an aqueous ion solution which is capable of forming an apatite.

BEST MODE FOR CARRYING OUT THE INVENTION

Figure 1:
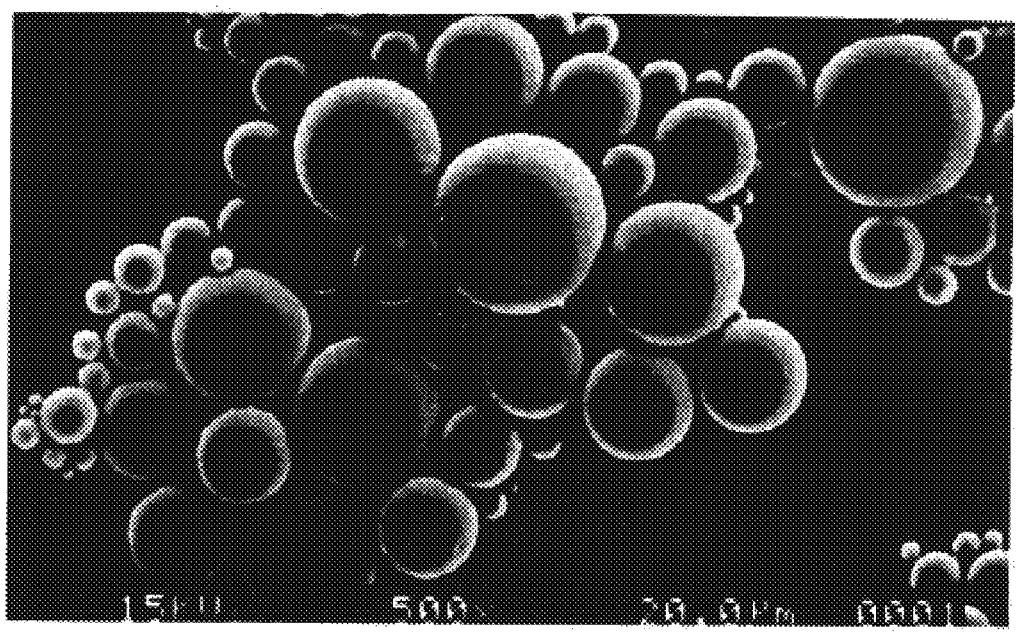
FIG. 1 is a scanning electron microphotograph of the microcapsules obtained in Reference Example 1.

The apatite for use in the present invention should only be a pharmacologically acceptable crystalline mineral and its composition is not particularly critical. However, the preferred apatite includes those minerals containing (1) at least one cation selected from the group consisting of $Na^+$, $K^+$, $H^+$, $Ca^{2+}$, $Sr^{2+}$, $Ba^{2+}$, $Pb^{2+}$, $Zn^{2+}$, $Cd^{2+}$, $Mg^{2+}$, $Fe^{2+}$, $Mn^{2+}$, $Ra^{2+}$, $Al^{3+}$, $Y^{3+}$, $Ce^{3+}$, $Nd^{3+}$, $La^{3+}$ and $Dy^{3+}$, and (2) at least one anion selected from the group consisting of $SO_4^{2-}$, $CO_3^{2-}$, $HPO_4^{2-}$, $PO_3F^{2-}$, $PO_4^{3-}$, $AsO_4^{3-}$, $VO_4^{3-}$, $BO_3^{3-}$, $CrO_4^{3-}$, $SiO_4^{3-}$, $GeO_4^{3-}$, $(CO_3F)^{3-}$ and $BO_4^{5-}$.

The apatite may further contain (3) at least one anion selected from the group consisting of $OH^-$, $F^-$, $Cl^-$, $Br^-$, $O^{2-}$, $CO_3^{2-}$ and $BO_2^-$.

As the preferable cation (1), mention is made of $Na^+$, $K^+$, $H^+$, $Ca^{2+}$, $Sr^{2+}$ or $Mg^{2+}$, more preferably $Ca^{2+}$, $Mg^{2+}$, especially preferably $Ca^{2+}$.

As the preferable anion (2), mention is made of $SO_4^{2-}$, $CO_3^{2-}$, $HPO_4^{2-}$, $PO_3F^{2-}$, $PO_4^{3-}$, more preferably $HPO_4^{2-}$, $PO_3F^{2-}$, $PO_4^{3-}$, especially preferably $PO_4^{3-}$.

As the preferable anion (3), mention is made of $OH^-$, $F^-$, $Cl^-$, $O^{2-}$ or $CO_3^{2-}$, more preferably $OH^-$, $F^-$ or $Cl^-$, especially preferably $OH^-$.

Usually, such apatites are made up of one cation species and one or two anion species. Thus, for example, crystalline minerals of the formula:

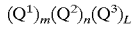
$$(Q^1)_m(Q^2)_n(Q^3)_L$$

wherein $Q^1$ denotes the cation (1) afore-mentioned, $Q^2$ denotes the anion (2) afore-mentioned, and $Q^3$ denotes the anion (3) afore-mentioned, are preferable.

m is an integer of 1 to 100, preferably 2 to 30, more preferably 5 to 15.

n is an integer of 1 to 50, preferably 1 to 20, more preferably 3 to 9.

L is an integer of 1 to 20, preferably 1 to 10, more preferably 1 to 3.

Furthermore, as the crystalline minerals, mention is made of those having the formula:

$$M_{10}(Z)_6X_2$$

wherein M denotes the cation (1) as mentioned above, Z denotes the anion (2) as mentioned above, and X denotes the anion (3) as mentioned above.

Preferred are hydroxyapatites in which $Q^3$ or X represents $OH^-$ and phosphate apatites in which $Q^2$ or X represents phosphate anion. The apatite may be a mixture of two or more species.

The biodegradable polymer employed in the present invention is a polymer that is hardly soluble or insoluble in water and degradable in a living body.

As the solubility of hardly soluble or insoluble in water, mention is made of 0 to 10 mg/ml, more preferably 0 to 1 mg/ml.

Examples of such biodegradable polymers include fatty acid polyesters such as polymers, copolymers and their mixture of one or more kinds of α-hydroxycarboxylic acids (e.g., lactic acid, glycolic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid), hydroxydicarboxylic acids (e.g., malic acid) and hydroxytricarboxylic acids (e.g., malic acid), lactic acid caprolactones, valerolactones, etc., and derivatives thereof (e.g., block polymers of polylactic acid, polyglycolic acid and polyethylene glycol), poly-α-cyanoacrylates, poly-β-hydroxybutyric acid, polyalkylene oxalates (e.g., polytrimethylene oxalate, polytetramethylene oxalate), polyortho-esters, polyortho-carbonates, polycarbonates (e.g., polyethylene carbonate, polyethylenepropylene carbonate), polyamino acids (e.g., poly-γ-benzyl-L-glutamic acid, poly-L-alanine, poly-γ-methyl-L-glutamic acid), hyarulonates, polystyrene, polymethacrylic acid, acrylic acid-methacrylic acid copolymers, dakin stearate, ethyl cellulose, acetyl cellulose, nitrocellulose, maleic anhydride copolymers, ethylene-vinyl acetate copolymers, polyvinyl acetate, polyacrylamide, collagen, gelatin and fibrin.

These biodegradable polymers may be in the form of homopolymers or copolymers of two or more kinds, or their mixtures.

Polymerization may be of the random, block or graft type.

Preferable biodegradable polymers include aliphatic polyesters.

From the viewpoint of biodegradability and biocompatibility, polymers and copolymers synthesized from one or more kinds of α-hydroxycarboxylic acids are preferred. Specifically, copolymers synthesized from one or more kinds of lactic acid, glycolic acid, 2-hydroxybutyric acid, 2-hydroxyvaleric acid etc., or mixtures thereof are used.

The biodegradable copolymer for the present invention can be produced by commonly known methods such as that described in European Patent Application Publication No. 172636 (Japanese Patent Application Laid-open No. 61-28521), or a modification thereof.

Although the above-mentioned α-hydroxycarboxylic acids may be of the D-, L- or D,L-configuration, the D,L-configuration is preferred.

Homopolymers of the above-mentioned α-hydroxycarboxylic acids include homopolymers of lactic acid, glycolic acid and 2-hydroxybutyric acid. The preferable α-hydroxycarboxylic acid is lactic acid. Copolymers of the above-mentioned α-hydroxycarboxylic acids include copolymers of glycolic acid and the other α-hydroxycarboxylic acids. Preferable α-hydroxycarboxylic acids are lactic acid and 2-hydroxybutyric acid. Specifically, useful copolymers include lactic acid-glycolic acid copolymers and 2-hydroxybutyric acid-glycolic acid copolymers, with preference given to polylactic acid-polyglycolic acid copolymers, etc.

The lower limit of the average molecular weight of these biodegradable polymers is preferably about 2,000, more preferably about 5,000.

The upper limit of the average molecular weight of the biodegradable polymers is preferably about 1,000,000, more preferably about 800,000, still more preferably about 500,000, especially preferably about 200,000.

The lower limit of the weight-average molecular weight of a lactic acid homopolymer (hereinafter also referred to as polylactic acid) is preferably about 5,000, preferably about 6,000.

The upper limit of the weight-average molecular weight of a lactic acid homopolymer is preferably about 10,000,000, more preferably about 5,000,000. Still more preferably about 100,000, especially preferably 50,000.

A polylactic acid can, for example, be synthesized by commonly known production methods such as that described in European Patent Application Publication No. 172636 (Japanese Patent Application Laid-open No. 61-28521).

The content ratio of lactic acid and glycolic acid in a polylactic acid or a lactic acid-glycolic acid copolymer is preferably from about 100/0 to 50/50 (w/w). The weight-average molecular weight of the lactic acid-glycolic acid copolymer is preferably about 5,000 to 100,000, more preferably about 8,000 to 50,000. The lactic acid-glycolic acid copolymer can be synthesized by a commonly known production method such as that described in European Patent Application Publication No. 172636 (Japanese Patent Application Laid-open No. 61-28521). The copolymer is preferably synthesized by catalyst-free dehydration polymerization condensation.

With respect to the 2-hydroxybutyric acid-glycolic acid copolymer, the content ratio is preferably such that glycolic acid accounts for about 40 to 70 mol %, and 2-hydroxybutyric acid accounts for the remaining portion.

The weight-average molecular weight of the 2-hydroxybutyric acid-glycolic acid copolymer is preferably about 5,000 to 100,000, more preferably about 8,000 to 50,000. The 2-hydroxybutyric acid-glycolic acid copolymer can be synthesized by a commonly known production method such as that described in European Patent Application Publication No. 172636 (Japanese Patent Application Laid-open No. 61-28521). The copolymer is preferably synthesized by catalyst-free dehydration polymerization condensation.

The above-described 2-hydroxybutyric acid-glycolic acid copolymer may be used in mixture with polylactic acid. When the 2-hydroxybutyric acid-glycolic acid copolymer is used in mixture with polylactic acid, the mixing ratio of 2-hydroxybutyric acid/glycolic acid is preferably about 10/90 to 90/10 (% by weight), more preferably about 15/85 to 85/15 (% by weight).

In the present specification, weight-average molecular weight is defined as that based on polystyrene measured by gel permeation chromatography (GPC). Measurements were taken using a GPC column KF804Lx2 (produced by Showa Denko, Japan) and an RI monitor L-3300 (produced by Hitachi Ltd., Japan) with chloroform as a mobile phase.

As the preferable biodegradable polymer, mention is made of polylactic acid, polyglycolic acid or a copolymer of polylactic acid and polyglycolic acid.

The medicinal substance which may be used in the present invention is preferably one which is hardly soluble or insoluble in water. The solubility is, for example, preferably 0 to 10 mg/ml, more preferably 0 to 1 mg/ml.

Since the apatite-coated pharmaceutical composition according to the present invention has a remarkable high affinity for bone, the medicinal substance for use in the present invention is preferably a medicine for prophylaxis or treatment of bone diseases, such as an osteoinductive factor, a bone resorption inhibiting agent, or a bone resorption promoter, although antitumor agents, antibiotics, antiinflammatory agents and anodynes, can also be used with advantage.

The medicinal substance for bone disease includes non-peptide osteoinductive substances such as prostaglandin Al derivatives, vitamin D derivatives, vitamin $K_2$ derivatives, eicosapentaenic acid derivatives, benzylphosphonic acid derivatives, bisphosporic acid derivatives, sex hormone derivatives, phenolsulfophthalein derivatives, benzothiepine derivatives, menatetrenone derivatives, helioxanthin derivatives, etc. and peptide osteoinductive factors such as bone morphogenetic protein (BMP) or its derivatives, cartilage derived growth factor (CDGF) or its derivatives, bone derived growth factor (BDGF) or its derivatives, transforming growth factor (TGF) or its derivatives, fibroblast growth factor (FGF) or its derivatives, skeleton growth factor (SGF) or its derivatives, tumor necrosis factor (TNF) or its derivatives, interferon (−α, −β, γ) or its derivatives, epidermal growth factor (EGF) or its derivatives, interleukin (−1, −2, −3, −6) or its derivatives, hepatocyte growth factor or its derivatives, carboxypeptidase-like protein or its derivatives, cathepsin k or its derivatives, calcitonin or its analogs, parathyroid hormone or its active fragments, growth hormone or its active fragments, estrogen or its active fragments.

The antibiotic that can be used includes but is not limited to aminoglycoside antibiotics such as amikacin, dibekacin, gentamicin, etc.

The anti-tumor agent includes anthracycline antineoplastic agents such as taxol, doxorubicin hydrochloride, methotrexate, etopoxide, 5-fluorouracil, mitoxantrone, mesna, dimesna, aminoglutethimide, tamoxifen, acrolein, cisplatin, carboplatin, cyclophosphamide, lomustin (CCNU), carmustin (BCNU).

The anti-inflammatory agent includes salicyclic acid derivatives represented by aspirin; pyrazolones represented by aminopyrine; anilides such as phenacetin, acetaminophen, etc.; pyrazolidinediones such as phenylbutazone, ketophenylbutazone, etc.; anthranilic acid compounds represented by mefenamic acid; acetic acid compounds represented by indomethacin; trioxopyrimidines represented by bucolome; basic anti-inflammatory compounds such as benzydamine, mepirizole, tiaramide, tinoridine, etc.; and anti-inflammatory enzymes, non-steroid anti-inflammatory drug.

The anodyne agents includes xylocaine, etc.

The medicinal substance may be formed as a pharmaceutically acceptable salt.

Pharmaceutically acceptable salts include salts with inorganic bases, salts with organic bases and salts with basic or acidic amino acids. Inorganic bases capable for forming such salts include alkali metals (e.g., sodium, potassium) and alkaline earth metals (e.g., calcium, magnesium), such organic bases include trimethylamine, triethylamine, pyridine, picoline, N,N-dibenzylethylenediamine and diethanolamine, such inorganic acids include hydrochloric acid, hydrobromic acid, hydroiodic acid, phosphoric acid, nitric acid and sulfuric acid, such organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid, and such basic or acidic amino acids include arginine, lysine, aspartic acid and glutamic acid.

Useful non-peptide osteogenetic promoting substances of the present invention include the sulfur-containing heterocyclic compounds such as (2R,4S)-(−)-N-[4-(Diethoxyphosphorylmethyl)phenyl]-1,2,4,5-tetrahydro-4-methyl-7,8-methylenedioxy-5-oxo-3-benzothiepine-2-carboxamide or salts thereof described in U.S. Pat. No. 5,071,841 (Japanese Patent Application Laid-open No. 3-232880), U.S. Pat. No. 5,158,943 (Japanese Patent Application Laid-open No. 4-364179 and Japanese Patent Application Laid-open No. 5-294960), or European Patent Application Publication No. 719782 (Japanese Patent Application Laid-open No. 8-225456), the benzopyrane derivatives such as N-(4-Dimethoxyphosphorylmethylphenyl)-4-oxo-4H-1-benzopyrane-2-carboxamide or salts thereof described in European Patent Application Publication No. 625522 (Japanese Patent Application Laid-open No. 7-291983), the phosphonic acid derivatives such as Diethyl 4-(7-cyclohexyl-3,4-dihydro-2-naphthalenecarboxamide) benzylphosphonate or salts thereof described in PCT International Patent Application Publication No. WO 96/01267 (Japanese Patent Application Laid-open No. 8-73476), the prostaglandin $A_1$ derivatives described in Journal of Pharmacology and Experimental Therapeutics, vol. 258, pp. 1120–1126 (1991), the vitamin $D_3$ derivatives described in the Bioorganic & Medicinal Chemistry Letters, vol. 3, pp. 1815–1819 (1993), the benzylphosphonic acid derivatives described in European Patent Application Publication No. 524023, the bisphosphonic acids described in Bone, vol. 13, pp. 249–255 (1992), and the vitamin $K_2$ derivatives described in Biochemical and Biophysical Research Communications, vol. 187, pp. 814–820 (1992).

In the above-mentioned non-peptide osteogenetic promoting substances, a compound represented by the following formula (I) or a salt thereof is preferably used for the present invention.

A compound of the formula (I):

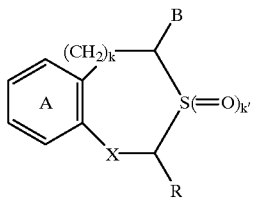

(I)

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and k' is 0, 1 or 2, or its salt.

With respect to the formula (I), the substituent of the substituted benzene represented by ring A is exemplified by halogen atoms, nitro groups, optionally substituted alkyl groups, optionally substituted hydroxy groups, optionally substituted mercapto groups, optionally substituted amino groups, acyl groups, mono- or di-alkoxyphosphoryl groups, phosphono groups, optionally substituted aryl groups, optionally substituted aralkyl groups and optionally substituted aromatic heterocyclic groups. Of these substituents, 1 to 4, preferably 1 or 2, whether identical or not, may be present on the benzene ring.

The halogen atoms include fluorine, chlorine, bromine and iodine.

The alkyl groups of the optionally substituted alkyl groups include alkyl groups having 1 to 10 carbon atoms such as methyl, ethyl, propyl, isopropyl, butyl, isobutyl, sec-butyl, tert-butyl, pentyl, isopentyl, neopentyl, hexyl, heptyl, octyl, nonyl and decyl, and cycloalkyl groups having 3 to 7 carbon atoms such as cyclopropyl, cyclobutyl, cyclohexyl and cycloheptyl. These alkyl groups may be substituted by 1 to 3 substituents selected from halogen atoms (e.g., fluorine, chlorine, bromine, iodine), hydroxy groups, alkoxy groups having 1 to 6 carbon atoms (e.g., methoxy, ethoxy, propoxy, butoxy, hexyloxy), mono- or di-$C_{1-6}$ alkoxyphosphoryl groups (e.g. methoxyphosphoryl, ethoxyphosphoryl, dimethoxyphosphoryl, diethoxyphosphoryl) and phosphono groups.

The substituted alkyl groups include trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, phosphono, phosphonomethyl and so on.

The substituted hydroxy groups include alkoxy groups, alkenyloxy groups, aralkyloxy groups, acyloxy groups, aryloxy groups and so on. Preferable alkoxy groups are alkoxy groups having 1 to 10 carbon atoms (e.g., methoxy, ethoxy, propoxy, butoxy, tert-butoxy, pentyloxy, hexyloxy, heptyloxy, nonyloxy) and cycloalkoxy groups having 4 to 6 carbon atoms (e.g., cyclobutoxy, cyclopentoxy, cyclohexyloxy). Preferable alkenyloxy groups are alkenyloxy groups having 2 to 10 carbon atoms such as allyloxy, crotyloxy, 2-pentenyloxy, 3-hexenyloxy, 2-cyclopentenylmethoxy and 2-cyclohexenylmethoxy. Preferable aralkyloxy groups are aralkyloxy groups having 6 to 19 carbon atoms, with greater preference given to $C_{6-14}$ aryl-$C_{1-4}$ alkyloxy groups (e.g., benzyloxy, phenethyloxy). Preferable acyloxy groups are alkanoyloxy groups such as those having 2 to 10 carbon atoms (e.g., acetyloxy, propionyloxy, n-butyryloxy, hexanoyloxy). Preferable aryloxy groups are aryloxy groups having 6 to 14 carbon atoms (e.g., phenoxy, biphenyloxy). Further, these groups may be substituted by 1 to 3 substituents selected from the above-mentioned halogen atoms, hydroxy groups, alkoxy groups having 1 to 6 carbon atoms, mono- or di-$C_{1-6}$ alkoxyphosphoryl groups, etc. The substituted hydroxyl groups include trifluoromethoxy, 2,2,2-trifluoroethoxy, difluoromethoxy, 2-methoxyethoxy, 4-chlorobenzyloxy and 2-(3,4-dimethoxyphenyl)ethoxy, and so on.

The substituted mercapto groups include alkylthio groups, aralkylthio groups and acylthio groups. Preferable alkylthio groups are alkylthio groups having 1 to 10 carbon atoms (e.g., methylthio, ethylthio, propylthio, butylthio, pentylthio, hexylthio, heptylthio, nonylthio) and cycloalkylthio groups having 4 to 6 carbon atoms (e.g., cyclobutylthio, cyclopentylthio, cyclohexylthio). Preferable aralkylthio groups are aralkylthio groups having 7 to 19 carbon atoms, more preferably $C_{6-14}$ aryl-$C_{1-4}$ alkylthio groups such as benzylthio and phenethylthio. Preferable acylthio groups are alkanoylthio groups such as those having 2 to 10 carbon atoms (e.g., acetylthio, propionylthio, n-butyrylthio, hexanoylthio). Further, these substituted thiol groups may be substituted by 1 to 3 substituents selected from the above-mentioned halogen atoms, hydroxy groups, alkoxy groups having 1 to 6 carbon atoms, mono- or di-$C_{1-6}$ alkoxyphosphoryl groups, etc. Specifically, the substituted thiol groups include trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio, and so on.

As substituents of the substituted amino groups, there may be used 1 or 2 identical or different substituents selected from the above-mentioned alkyl groups having 1 to 10 carbon atoms, alkenyl groups having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups having 6 to 14 carbon atoms and aralkyl groups having 7 to 19 carbon atoms. These substituents may be substituted by the above-mentioned halogen atoms, alkoxy groups having 1 to 6 carbon atoms, mono- or di-$C_{1-6}$ alkoxyphosphoryl groups, phosphono groups, etc. Specifically, the substituted amino groups include methylamino, dimethylamino, ethylamino, diethylamino, dibutylamino, diallylamino, cyclohexylamino, phenylamino, N-methyl-N-phenylamino, N-methyl-N-(4-chlorobenzyl)amino and N,N-di(2-methoxyethyl)amino, and so on.

The acyl groups include organic carboxylic acid acyl groups and sulfonic acid acyl groups with a hydrocarbon group having 1 to 6 carbon atoms (e.g., methyl, ethyl, n-propyl, hexyl, phenyl). Useful organic carboxylic acyl groups are formyl, $C_{1-10}$ alkyl-carbonyl groups (e.g., acetyl, propionyl, butyryl, valeryl, pivaloyl, hexanoyl, octanoyl, cyclobutanecarbonyl, cyclohexanecarbonyl, cycloheptanecarbonyl), $C_{2-10}$ alkenyl-carbonyl groups (e.g., crotonyl, 2-cyclohexenecarbonyl), $C_{6-14}$ aryl-carbonyl groups (e.g., benzoyl), $C_{7-19}$ aralkyl-carbonyl groups (e.g., benzylcarbonyl, benzhydrylcarbonyl), 5- or 6-membered aromatic heterocyclic carbonyl groups (e.g, nicotinoyl, 4-thiazolylcarbonyl) and 5- or 6-membered aromatic heterocyclic acetyl groups (e.g., 3-pyridylacetyl, 4-thiazolylacetyl). Useful sulfonic acyl groups having 1 to 6 carbon atoms are methanesulfonyl and ethanesulfonyl. These acyl groups may be substituted by 1 to 3 substituents selected from the above-mentioned halogen atoms, hydroxyl groups, alkoxy groups having 1 to 6 carbon atoms, amino groups, etc. Specifically, the substituted acyl groups include trifluoroacetyl, trichloroacetyl, 4-methoxybutyryl, 3-cyclohexyloxypropionyl, 4-chlorobenzoyl and 3,4-dimethoxybenzoyl, and so on.

The mono- or di-alkoxyphosphoryl groups include mono-$C_{1-6}$ alkoxyphosphoryl groups such as methoxyphosphoryl, ethoxyphosphoryl, propoxyphosphoryl, isopropoxyphosphoryl, butoxyphosphoryl, pentyloxyphosphoryl and hexyloxyphosphoryl, and di-$C_{1-6}$ alkoxyphosphoryl groups such as dimethoxyphosphoryl, diethoxyphosphoryl, dipropoxyphosphoryl, diisopropoxyphosphoryl, dibutoxyphosphoryl, dipentyloxyphosphoryl and dihexyloxyphosphoryl, with preference given to di-$C_{1-6}$ alkoxyphosphoryl groups such as dimethoxyphosphoryl, diethoxyphosphoryl, dipropoxyphosphoryl, diisopropoxyphosphoryl, ethylenedioxyphosphoryl, dibutoxyphosphoryl, etc.

The aryl groups of the optionally substituted aryl groups include aryl groups having 6 to 14 carbon atoms such as phenyl, naphthyl and anthryl. These aryl groups may be substituted by 1 to 3 substituents selected from the above-mentioned alkyl groups having 1 to 10 carbon atoms, halogen atoms, hydroxyl groups, alkoxy groups having 1 to 6 carbon atoms, etc. Specifically, the substituted aryl groups include 4-chlorophenyl, 3,4-dimethoxyphenyl, 4-cyclohexylphenyl and 5,6,7,8-tetrahydro-2-naphthyl.

The aralkyl groups of the optionally substituted aralkyl groups include aralkyl groups having 7 to 19 carbon atoms such as benzyl, naphthylethyl and trityl. These aralkyl groups may be substituted by 1 to 3 substituents selected from the above-mentioned alkyl groups having 1 to 10 carbon atoms, halogen atoms, hydroxy groups, alkoxy groups having 1 to 6 carbon atoms, etc. on the aromatic ring. Specifically, the substituted aralkyl groups include 4-chlorobenzyl, 3,4-dimethoxybenzyl, 4-cyclohexylbenzyl and 5,6,7,8-tetrahydro-2-naphthylethyl.

The aromatic heterocyclic groups of the optionally substituted aromatic heterocyclic groups include 5- to 6-membered aromatic heterocyclic groups having 1 to 4 atoms of nitrogen, oxygen and/or sulfur, such as furyl, thienyl, imidazolyl, thiazolyl, oxazolyl and thiadiazolyl. These aromatic heterocyclic groups may be substituted by 1 to 3 substituents selected from the above-mentioned alkyl groups having 1 to 10 carbon atoms, halogen atoms, hydroxy groups, alkoxy groups having 1 to 6 carbon atoms, etc.

Provided that two alkyl groups are present as mutually adjoining substituents on the benzene ring A, they may bind together to form an alkylene group represented by the formula: —$(CH_2)_m$— wherein m is an integer from 3 to 5 (e.g., trimethylene, tetramethylene, pentamethylene). Provided that two alkoxy groups are present as mutually adjoining substituents on the benzene ring A, they may bind together to form an alkylenedioxy group represented by the formula; —O—$(CH_2)_n$—O— wherein n is an integer from 1 to 3 (e.g., methylenedioxy, ethylenedioxy, trimethylenedioxy). In these cases, a 5- to 7-membered ring is formed in cooperation with carbon atoms of the benzene ring.

With respect to the formula (I), R is a hydrogen atom or an optionally substituted hydrocarbon group.

The hydrocarbon group of the optionally substituted hydrocarbon group represented by R is exemplified by the above-mentioned alkyl groups (preferably alkyl groups having 1 to 10 carbon atoms), alkenyl groups (preferably alkenyl groups having 2 to 10 carbon atoms), aryl groups (preferably aryl groups having 6 to 14 carbon atoms) and aralkyl groups (preferably aralkyl groups having 7 to 19 carbon atoms). Useful substituents on the hydrocarbon group include the above-mentioned 5- or 6-membered aromatic heterocyclic groups, halogen atoms, di-$C_{1-6}$ alkoxyphosphoryl groups and phosphono groups.

Preferable examples of R are an unsubstituted alkyl groups having 1 to 6 carbon atoms such as methyl, ethyl, propyl, isopropyl, butyl, isobutyl, sec-butyl, tert-butyl, pentyl, neopentyl and hexyl.

With respect to the formula (I), B is an optionally esterified or amidated carboxyl group.

The esterified carboxyl group represented by B is exemplified by alkoxycarbonyl group, preferably $C_{1-10}$ alkoxycarbonyl groups (e.g., methoxycarbonyl, ethoxycarbonyl, propoxycarbonyl, butoxycarbonyl), aryloxy-carbonyl groups, preferably $C_{6-14}$ aryloxy-carbonyl groups (e.g., phenoxycarbonyl), and aralkyloxycarbonyl groups, preferably $C_{7-19}$ aralkyloxy-carbonyl groups (e.g., benzyloxycarbonyl).

The amidated carboxyl group represented by B is exemplified by an optionally substituted carbamoyl group represented by the formula: —CON($R_1$)($R_2$) wherein $R_1$ and $R_2$ independently are a hydrogen atom, an optionally substituted hydrocarbon group or an optionally substituted 5- to 7-membered heterocyclic group.

The hydrocarbon group of the optionally substituted hydrocarbon group represented by $R_1$ or $R_2$ is exemplified by the above-mentioned alkyl groups, preferably alkyl groups having 1 to 10 carbon atoms (e.g., methyl, ethyl, propyl, isopropyl, butyl, isobutyl, sec-butyl, tert-butyl, pentyl, isopentyl, neopentyl, hexyl, heptyl, octyl, nonyl, decyl), alkenyl groups, preferably those having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups, preferably those having 6 to 14 carbon atoms (e.g., phenyl, naphthyl, anthryl), and aralkyl groups, preferably those having 7 to 19 carbon atoms (e.g., benzyl, naphthyl, trityl). These hydrocarbon groups may be substituted by 1 to 3 substituents selected from (i) halogen atoms (e.g., fluorine, chlorine, bromine, iodine), (ii) hydroxyl groups, (iii) alkoxy groups having 1 to 6 carbon atoms (e.g., methoxy, ethoxy, propoxy, butoxy, tert-butoxy, pentyloxy, hexyloxy), (iv) amino groups which may be substituted by alkyl groups (e.g., methyl, ethyl, propyl, isopropyl, butyl, isobutyl, sec-butyl, tert-butyl, pentyl, isopentyl, neopentyl, hexyl) having 1 to 6 carbon atoms (e.g., amino, methylamino, ethylamino, dimethylamino, diethylamino, dipropylamino), (v) amino groups substituted by $C_{1-10}$ acyl groups (e.g., acetylamino, propionylamino, benzoylamino), (vi) carbamoyl groups which may be substituted by alkyl groups having 1 to 6 carbon atoms (e.g., carbamoyl, methylcarbamoyl, dimethylcarbamoyl, diethylcarbamoyl), (vii) $C_{1-6}$ alkoxy-carbonyl groups (e.g., methoxycarbonyl, ethoxycarbonyl, propoxycarbonyl), (viii) mono- or di-alkoxyphosphoryl groups (e.g. mono- or di-$C_{1-6}$ alkoxyphosphoryl groups such as dimethoxyphosphoryl, diethoxyphosphoryl, ethylenedioxyphosphoryl), (ix) mono- or di-alkoxyphosphorylalkyl groups (e.g. mono- or di-$C_{1-6}$ alkoxyphosphoryl-$C_{1-3}$ alkyl groups such as methoxyphosphorylmethyl, ethoxyphosphorylmethyl, methoxyphosphorylethyl, ethoxyphosphorylethyl, dimethoxyphosphorylmethyl, diethoxyphosphorylmethyl, dimethoxyphosphoryethyl, diethoxyphosphoryethyl), (x) a moiety:

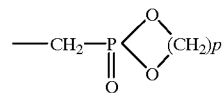

wherein p is an integer from 2 to 4, (xi) phosphono groups, (xii) the above-mentioned aromatic heterocyclic groups, etc.

The 5- to 7-membered heterocyclic group of the optionally substituted 5- to 7-membered heterocyclic group represented by $R_1$ or $R_2$ is exemplified by 5- to 7-membered heterocyclic groups containing a sulfur, nitrogen or oxygen atom, 5- or 6-membered heterocyclic groups containing 2 to 4 nitrogen atoms, and 5- or 6-membered heterocyclic groups containing 1 or 2 nitrogen atom(s) and a sulfur or oxygen atom. These heterocyclic groups may be condensed with a 6-membered ring containing 2 or fewer nitrogen atoms, a benzene ring or a 5-membered ring containing a sulfur atom.

As substituents of the substituted 5- to 7-membered heterocyclic group represented by $R_1$ and $R_2$, there may be used 1 to 4 of the same substituents as those for the substituted hydrocarbon group represented by $R_1$ and $R_2$ above.

Preferable examples of the 5- to 7-membered heterocyclic group represented by $R_1$ and $R_2$ include 2-pyridyl, pyrimidyl, pyrazinyl, pyridazinyl, pyrazolyl, imidazolyl, thiazolyl, oxazolyl, tetrazolylt thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl and morpholino, pyrido[2,3-d]pyrimidyl, benzopyranyl, 1,8-naphthyridyl, quinolyl, thieno[2,3-b]pyridyl.

The moiety: —N$R_1$($R_2$) may form a 5- to 7-membered ring by binding together with $R_1$ and $R_2$. Such rings include morpholine, piperidine, thiomorpholine, homopiperidine, piperidine, pyrrolidine, thiazolidine and azepine.

The substituted alkyl groups as preferable examples of the optionally substituted hydrocarbon group represented by $R_1$ and $R_2$ include trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N-ethylamino) ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tert-butoxycarbonylpropyl, 2-diethoxyphosphorylethyl, 3-dipropoxyphosphorylpropyl, 4-dibutoxyphosphorylbutyl, ethylenedioxyphosphorylmethyl, 2-phosphonoethyl and 3-phosphonopropyl. The preferable substituted aralkyl groups include 4-chlorobenzyl, 3-(2-fluorophenyl)propyl, 3-methoxybenzyl, 3,4-dimethoxyphenethyl, 4-ethylbenzyl, 4-(3-trifluoromethylphenyl)butyl, 4-acetylaminobenzyl, 4-dimethylaminophenethyl, 4-diethoxyphosphorylbenzyl and 2-(4-dipropoxyphosphorylmethylphenyl)ethyl. The preferable substituted aryl groups include 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-diethoxyphosphorylmethylphenyl, 4-dipropoxyphosphorylphenyl, 4-(2-phosphonoethyl) phenyl, 4-phosphonomethylphenyl and 4-phosphonophenyl. The preferable substituted 5- to 7-membered heterocyclic groups include 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 3-methyl-2-thienyl, 4,5-dimethyl-2-furanyl and 4-methyl-2-morpholinyl.

With respect to the formula (I), ring A is preferably a benzene ring which may be substituted by 1 or more, more preferably 1 or 2 substituents selected from ① halogen atoms, ② optionally substituted alkyl groups, ③ optionally substituted hydroxy groups, ④ optionally substituted thiol groups and/or ⑤ optionally substituted amino groups.

More preferably, ring A is a benzene ring which may be substituted by 1 or 2 substituents selected from the above-mentioned halogen atoms, alkyl groups having 1 to 10 carbon atoms (furthermore preferably 1 to 5 carbon atoms), alkoxy groups having 1 to 10 carbon atoms (furthermore preferably 1 to 5 carbon atoms), alkylenedioxy groups represented by the formula: —O—$(CH_2)_n$—O— wherein n is an integer from 1 to 3, and/or alkylthio groups having 1 to 10 carbon atoms (furthermore preferably 1 to 5 carbon atoms).

Most preferably, ring A is a benzene ring which may be substituted by an alkylenedioxy group represented by the formula: —O—$(CH_2)_n$—O— wherein n is an integer from 1 to 3.

B is preferably an alkoxy-carbonyl group or a group represented by the formula: —$CON(R_1)(R_2)$ wherein $R_1$ and $R_2$ independently are a hydrogen atom, an optionally substituted hydrocarbon group or an optionally substituted 5- to 7-membered heterocyclic group.

With respect to $R_1$ and $R_2$ above, $R_1$ is preferably a hydrogen atom or an alkyl group having 1 to 10 carbon atoms (e.g. methyl, ethyl, propyl), and $R_2$ is preferably a phenyl or phenyl-$C_{1-3}$ alkyl group which may be substituted by a halogen atom (e.g. fluorine, chlorine, bromine), a $C_{1-6}$ alkoxy (e.g. methoxy, ethoxy), a mono- or di-alkoxyphosphoryl (preferably a mono- or di-$C_{1-6}$ alkoxyphosphoryl such as diethoxyphosphoryl), a mono- or di-alkoxyphosphorylalkyl (preferably a mono- or di-$C_{1-6}$ alkoxyphosphoryl-$C_{1-3}$ alkyl such as diethoxyphosphorylmethyl) or a $C_{1-6}$ alkoxycarbonyl (e.g. methoxycarbonyl, ethoxycarbonyl), or a 5- or 6-membered heterocyclic group (e.g. pyridyl) which may be substituted by a phenyl and that contains 1 or 2 nitrogen atom(s) or a nitrogen atom and a sulfur atom.

A more preferable example of $R_1$ and $R_2$ is "$R_1$ is a hydrogen atom, and $R_2$ is a phenyl group substituted by a mono- or di-$C_{1-6}$ alkoxyphosphoryl-$C_{1-3}$ alkyl (e.g. 4-diethoxyphosphorylmethylphenyl)".

With respect to the formula (I), X is —CH(OH)— or —CO—, preferably —CO—.

With respect to the formula (I), k is 0 or 1, and k' is 0, 1 or 2, preferablly k is 1, and k' is 0.

R is preferably a hydrogen atom, an alkyl group having 1 to 6 carbon atoms (e.g. methyl, ethyl) or a phenyl group.

The compound (I) is preferably an optically active compound represented by the formula (II):

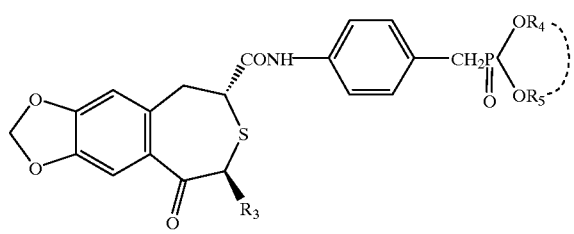

wherein $R_3$ is a lower alkyl group; $R_4$ and $R_5$ independently are a lower alkyl group or bind together to form a lower alkylene group.

The lower alkyl group represented by $R_3$, $R_4$ or $R_5$ in the formula (II) is exemplified by alkyl groups having 1 to 6 (preferably 1 to 4) carbon atoms such as methyl, ethyl, propyl, isopropyl, butyl, isobutyl, sec-butyl, tert-butyl, pentyl, isopentyl, neopentyl and hexyl. $R_4$ and $R_5$ may bind together to form a lower alkylene group. In this case, a moiety:

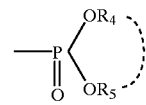

may represent a moiety:

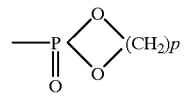

wherein p is an integer from 2 to 4.

Preferable groups for $R_3$, $R_4$ and $R_5$ include alkyl groups having 1 to 4 carbon atoms such as methyl and ethyl.

The compound (II) is an optically active compound of the (2R,4S) configuration, and contains substantially no compound of the (2S,4R) configuration. The compound (II) of which optical purity is nearly 100% is preferable.

Most preferably, the compound (II) is, for example, (2R,4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide (hereinafter also referred to as Compound A).

The salt of a non-peptide osteogenetic promoting substance of the present invention is preferably a pharmaceutically acceptable salt. Pharmaceutically acceptable salts include salts with inorganic bases, salts with organic bases and salts with basic or acidic amino acids. Inorganic bases capable for forming such salts include alkali metals (e.g., sodium, potassium) and alkaline earth metals (e.g., calcium, magnesium), such organic bases include trimethylamine, triethylamine, pyridine, picoline, N,N-dibenzylethylenediamine and diethanolamine, such inorganic acids include hydrochloric acid, hydrobromic acid, hydroiodic acid, phosphoric acid, nitric acid and sulfuric acid, such organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid, and such basic or acidic amino acids include arginine, lysine, aspartic acid and glutamic acid.

The non-peptide osteogenetic promoting substance of the sulfur-containing heterocyclic compounds for the use of the present invention can be produced by, for example, the methods described in U.S. Pat. Nos. 5,071,841, 5,158,943, Japanese Patent Applications Laid-open Nos. 5-294960, EP-719782 and WO 97/03989. The other compounds for the use of the present invention can be produced in a manner described in Japanese Patent Application Laid-open No. 7-291983, WO 96/01267, EP-524023.

In accordance with the present invention, a substrate, i.e. (1) a solid composition containing a biodegradable polymer or (2) a solid composition containing a biodegradable polymer and a medicinal substance, is immersed in an apatite-forming buffer solution so as to coat the surface of the substrate with apatite.

The substrate is preferably used in a granular form (granules, fine granules, fine particles) but its geometry is not so critical. When it is molded into granules or an equivalent form, the particle diameter is preferably about 0.1 nm to about 10000 μm, more preferably about 1 nm to about 1000 μm, still more preferably about 5 nm to about 500 μm, most preferably about 10 nm to 200 μm.

The medicinal substance for use in the present invention can be produced by the process described in the patent gazette mentioned hereinbefore or any process analogous thereto. In the present invention, the medicinal substance is employed before molding with the aid of a suitable excipient into a desired form.

The excipient mentioned above is a biocompatible and water-insoluble substance. Examples of such excipient are starch or its derivatives, calcium sulfate hemihydrate (Plaster of Paris), bone wax (ex. a mixture of beesmax and isopropylpalmitate), α-tricalcium phosphate (α-TCP), β-tricalcium phosphate (β-TCT), polyethyleneglycol, hydroxyapatite, polymethylmethacrylate, poloxamers.

The water-soluble medicinally active substance may be enclosed in such an insoluble excipient.

The ratio of the biodegradable polymer to the medicinal substance, when these two are employed as a substrate, is preferably about 0.1 to 10,000 times, more preferably about 0.2 to 500 times, still more preferably 0.5 to 50 times. (The ratio is the biodegradable polymer/the medicinal substance.)

When the medicinal substance is compound (I), for instance, the amount of the biodegradable polymer relative to compound (I) is about 0.2 to 10,000 times (by weight), preferably about 1 to 1,000 times (by weight), and more preferably about 1 to 100 times (by weight).

When a composition containing a biodegradable polymer is used as the substrate, the composition molded from one or more than one species of said biodegradable polymer or the composition molded after addition of the medicinal substance can be used. When a medicinal substance is included, the amount of the biodegradable polymer may be adjusted with reference to the strength of pharmacological activity of the medicinal substance and the designed rate and duration of release of the medicinal substance from the biodegradable polymer.

The substrate for the use in the present invention, i.e. (1) a solid composition containing a biodegradable polymer or (2) a solid composition containing a biodegradable polymer and a medicinal substance, can be produced by per se known conventional methods of producing a pharmaceutical composition, for example, it can be produced by dispersing a medicinal substance in a biodegradable polymer, or by filling a previously shaped hollow biodegradable polymer with a medicinal substance. Specifically, useful methods include the in-water drying method, the phase separation method, the spray drying method, the heat-molding method and modifications thereof.

The shape of the substrate for the use of the present invention as obtained by a production method mentioned above may be in the form of, for example, fine particles, spheres, rods, needles, pellets, films or creams, but the shape is not limited thereto as long as the desired purpose is accomplished.

In the present invention, the substrate and the desired pharmaceutical solid composition of fine particles is preferably a microcapsule or a microsphere.

Example methods of producing microcapsules are described below.

(1) In-water Drying Method (O/W Method)

In this method, an organic solvent solution comprising a biodegradable polymer is first prepared. The organic solvent used to produce the pharmaceutical composition of the present invention preferably has a boiling point of not higher than 120° C. Such organic solvents include halogenated hydrocarbons (e.g., dichloromethane, chloroform, chloroethane, dichloroethane, trichloroethane, carbon tetrachloride), aliphatic esters (e.g., ethyl ester, butyl ester), ethers (e.g., ethyl ether, isopropyl ether) and aromatic hydrocarbons (e.g., benzene, toluene, xylene). These solvents may be used in combination of two or more kinds in appropriate ratios. The organic solvent is preferably dichloromethane or acetonitrile, more preferably dichloromethane. The concentration of biodegradable polymer in the organic solvent solution is normally chosen over the range of about 0.01 to 80% (w/w), preferably about 0.1 to 70% (w/w), and more preferably about 1 to 60% (w/w), although varying depending on molecular weight of biodegradable polymer and organic solvent type, etc.

When the medicinal substance is added, it is added and dissolved into the organic solvent solution comprising the biodegradable polymer thus obtained, if necessary after the medicinal substance is lyophilized or vacuum dried. The amount of the medicinal substance is about 0.001 to 90% (w/w), preferably about 0.01 to 80% (w/w), and more preferably about 0.1 to 50% (w/w), based on the concentration of biodegradable polymer in the organic solvent solution, although varying depending on, e.g. drug type, mechanism of action, effect duration.

The organic solvent solution thus prepared is then added to an aqueous phase to form an O/W emulsion using a turbine type mechanical stirrer or the like. The volume ratio of the aqueous phase to the oil phase is normally chosen from the range of about 1 to 10,000, preferably about 2 to 5,000, and more preferably about 5 to 2,000.

An emulsifier may be added to the aqueous phase. The emulsifier may be any one as long as it is capable of forming a stable O/W emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used in combination as appropriate. The concentration of emulsifier in the aqueous phase is preferably about 0.001 to 20% (w/w), more preferably about 0.01 to 10% (w/w), and further more preferably about 0.05 to 5% (w/w).

Solvent evaporation from the oil phase can be achieved by commonly used methods, including the method in which the solvent is evaporated under normal or gradually reduced pressure during stirring using a propeller stirrer or magnetic stirrer, etc., and the method in which the solvent is evaporated while the degree of vacuum is adjusted using a rotary evaporator, etc. The obtained microcapsules are separated by centrifugal method or filtration, after which they are washed with, for example, water or heptane, several times to remove the medicinal substances, emulsifier, etc. adhering to the microcapsule surface. The microcapsules are then again dispersed in distilled water, etc. and lyophilized.

In addition to the above-described O/W method, microcapsules may be produced by the S/O/W method, which is mentioned below, in which a medicinal substance is dispersed in an organic solvent solution comprising a biodegradable polymer.

(2) In-water Drying Method (S/O/W Method)

In this method for producing microcapsules containing a medicinal substance which is hardly soluble in water or insoluble in water, at first, a biodegradable polymer solution in an organic solvent (oil phase), are prepared in accordance with the methods of those described in the in-water drying method mentioned in the above item (1).

To thus obtained solution, fine particles of the medicinal substance are added, followed by stirring, to give a S/O suspension. The stirring is carried out with per se known conventional suspension method, such as shaking method, homogenizing method, ultrasonication, etc.

Thus obtained S/O suspension is poured into an aqueous phase to produce S/O/W emulsion, and the solvent in the oily phase is evaporated off, in a similar manner to the methods of the above (1), to give microcapsules.

(3) Phase Separation Method

In this method, a coacervating agent is gradually added to the above-described W/O emulsion under stirring to precipitate and solidify the biodegradable polymer. The coacervating agent used can be silicon oil, vegetable oils and fats (e.g., sesame oil, soybean oil, corn oil, cotton seed oil, coconut oil, linseed oil), mineral oils, hydrocarbons (e.g., n-hexane, n-heptane), as long as it is a polymeric, mineral oil or vegetable oil compound which can be mixed with the solvent of the biodegradable polymer and which does not dissolve the polymer for encapsulation. These coacervating agents may be be used in combination of two or more kinds.

After filtration and separation, the obtained microcapsules are repeatedly washed with heptane, etc. to remove the coacervating agent. The free drug and solvent are then removed in the same manner as in-water drying method. To prevent particle flocculation during washing, antiflocculants: water-soluble sugars such as mannitol, lactol, glucose and starches (e.g., corn starch), amino acids such as glycine and alanine, and proteins such as gelatin, fibrin and collagen may be added.

(4) Spray Drying Method

For producing microcapsules by this method, the above-described W/O emulsion is sprayed via a nozzle into the drying chamber of a spray drier to volatilize the organic solvent and water into the fine droplets in a very short time, to obtain microcapsules. The nozzle is exemplified by the double-fluid nozzle, pressure nozzle and rotary disc nozzle. To prevent microcapsule flocculation, an aqueous solution of the above-described antiflocculant may be sprayed via another nozzle, while the W/O emulsion is sprayed. The microcapsules thus obtained may be warmed under reduced pressure to facilitate the removal of the water and solvent contained in them.

In addition to the above-described microcapsules, the pharmaceutical composition of the present invention can be produced by dissolving a biodegradable polymer in which a medicinal substance is dispersed, and forming the solution into spheres, rods, needles, pellets, films or the like, by an appropriate method. The biodegradable polymer dispersed medicinal substance is produced in accordance with, for example, the method described in U.S. Pat. No. 3,773,919 (Japanese Patent Publication No. Sho 50-17525).

Furthermore, the pharmaceutical composition of the present invention can also be produced by pulverizing to appropriate particle size a biodegradable polymer dispersed medicinal substance by a method such as that described in Japanese Patent Application Laid-open No. 6-234656, which employs a turbo counter jet mill pulverizer or an ultrasonic jet pulverizer. Specifically, the medicinal substance is added to an organic solvent containing the biodegradable polymer, and dissolved therein. The solid solution obtained by vacuum drying is then coarsely pulverized and sieved, followed by solvent removal, after which the coarse particles are pulverized to a controlled particle size using an ultrasonic jet pulverizer, to yield the pharmaceutical composition of the present invention.

In accordance with the present invention, the substrate for the use in the present invention, i.e. (1) a solid composition containing a biodegradable polymer or (2) a solid composition containing a biodegradable polymer and a medicinal substance, is immersed in, or otherwise contacted with, an aqueous ion solution at a predetermined temperature for a predetermined time to thereby coat the surface of the composite with apatite.

The composition of the aqueous ion solution for use in the present invention is not particularly restricted as long as it is capable of forming an apatite and can be selected according to the desired composition of apatite.

As the aqueous ion solution, mention is made of an aqueous solution containing (1) at least one cation selected from the group consisting of $Na^+$, $K^+$, $H^+$, $Ca^{2+}$, $Sr^{2+}$, $Ba^{2+}$, $Pb^{2+}$, $Zn^{2+}$, $Cd^{2+}$, $Mg^{2+}$, $Fe^{2+}$, $Mn^{2+}$, $Ra^{2+}$, $Al^{3+}$, $Y^{3+}$, $Ce^{3+}$, $Nd^{3+}$, $La^{3+}$ and $Dy^{3+}$, and (2) at least one anion selected from the group consisting of $SO_4^{2-}$, $CO_3^{2-}$, $HPO_4^{2-}$, $PO_3F^{2-}$, $PO_4^{3-}$, $AsO_4^{3-}$, $VO_4^{3-}$, $BO_3^{3-}$, $CrO_4^{3-}$, $SiO_4^{3-}$, $GeO_4^{3-}$, $(CO_3F)^{3-}$ and $BO_4^{5-}$.

The aqueous ion solution may contain (3) at least one anion selected from the group consisting of $OH^-$, $F^-$, $Cl^-$, $Br^-$, $O^{2-}$, $CO_3^{2-}$ and $BO_2^-$.

As the preferable cation (1), mention is made of $Na^+$, $K^+$, $H^+$, $Ca^{2+}$ or $Mg^{2+}$, more preferably $Ca^{2+}$, $Mg^{2+}$, especially preferably $Ca^{2+}$.

As the preferable anion (2), mention is made of $SO_4^{2-}$, $CO_3^{2-}$, $HPO_4^{2-}$, $PO_3F^{2-}$, $PO_4^{3-}$, $SiO_4^{3-}$ or $(CO_3F)^{3-}$, more preferably $HPO_4^{2-}$, $PO_3F^{3-}$, $PO_4^{3-}$, especially preferably $PO_4^{3-}$.

As the preferable anion (3), mention is made of $OH^-$, $F^-$, $Cl^-$ or $O^{2-}$, more preferably $OH^-$, $F^-$ or $Cl^-$, especially preferably $OH^-$.

In particular, combinations of body fluid component ions such as $Na^+$, $K^+$, $Mg^{2+}$, $Ca^{2+}$, $Cl^-$, $CO_3^{2-}$, $PO_4^{3-}$, and $SO_4^{2-}$ are preferably used. Combinations with other ions are also permissible and, if necessary, unnecessary ions may be eliminated from the above-mentioned ion species in the preparation of an aqueous solution of ions for coating.

The concentration of the cation (1) in the aqueous solution is preferably about 0.01 to about 1000 mM, more preferably about 0.02 to about 500 mM. The concentration of the anion (2) in the aqueous solution is preferably about 0.005 to about 1000 mM, more preferably about 0.01 to about 500 mM. The concentration of the anion (3) in the aqueous solution is preferably about 0.1 to about 1000 mM, more preferably about 0.2 to about 500 mM.

Specifically, the ion concentration for sodium ion is preferably about 50 to 300 mM and most preferably about 100 to 180 mM. The ion concentration for potassium ion is preferably about 1 to 50 mM and most preferably about 2 to 15 mM. The ion concentration for magnesium ion is preferably about 0.1 to 10 mM and most preferably about 0.5 to 4 mM. The ion concentration for calcium ion is preferably about 0.4 to 40 mM and most preferably about 0.5 to 20 mM. The ion concentration for chloride ion is preferably about 50 to 300 mM and most preferably about 100 to 200 mM. The ion concentration for carbonate ion is preferably about 0.5–100 mM and most preferably about 1 to 50 mM. The ion concentration for phosphate ion is preferably about 0.05 to 20 mM and most preferably about 0.2 to 10 mM. The ion concentration for sulfate ion is preferably about 0.03 to 10 mM and most preferably about 0.1 to 5 mM.

Moreover, a substance not charged in water (e.g. mannitol) may be added to such a combination of ions. In addition, such third components as a stabilizer, a preservative, an isotonizing agent, etc. can also be added. In order to carry out apatite coating aseptically, bactericidal or bacteriostatic agents such as thimerosal or ethanol can be added.

The immersion time of the substrate in the aqueous ion solution for coating can be adjusted according to the desired thickness of the coating layer. The longer the duration of contact with the aqueous ion solution is, the greater is the thickness of the apatite layer formed.

The immersing time for forming an apatite layer of about 1 nm to 50 $\mu$m is preferably about 1 hour to 30 days, that for forming an apatite layer of about 1 nm to 30 $\mu$m is preferably about 1 hour to 20 days, that for forming an apatite layer of about 1 nm to 20 $\mu$m is preferably about 1 hour to 15 days, that for forming an apatite layer of about 1 nm to 10 $\mu$m is preferably about 1 hour to 10 days.

The coating time can also be adjusted according to the condition of the substrate to be coated with apatite. For example, a rough substrate surface rather than a smooth surface can be coated in a shorter time.

In the present invention, the temperature of the aqueous ion solution upon contact with, or immersion in, can also be freely selected but is generally about 10 to 150° C., preferably about 30 to 130° C., more preferably about 30 to 50° C., and most preferably about 35 to 38° C. The optimum temperature can be selected in view of the stability of the polymer and medicinally active substance in the substrate against temperature.

The pH of the aqueous ion solution can also be freely selected. However, for purposes of the present invention, it is generally pH about 1 to 14, preferably pH about 5 to 10, and more preferably pH about 6.5 to 8.5.

The pH of the aqueous ion solution can be optimized with reference to the dissolution equilibrium of apatite and the influence on the stability of the substrate polymer and/or medicinally active substance.

In the present invention, the term "coating" is used to mean that the surface of the solid composition containing the biodegradable polymer or the solid composition containing the biodegradable polymer and the medicinal substance is thoroughly covered with an apatite layer. However, this apatite layer may be porous or need not necessarily be uniform in thickness. From the standpoint of drug release characteristics, the apatite layer is preferably a honeycomb layer. In particular, when the apatite comprises a calcium ion and a phosphate ion, the apatite layer formed is preferably a honeycomb layer.

In the present invention, the thickness of the apatite layer is generally about 1 nm to about 50 $\mu$m, and when the substrate comprises microspheres or the like, is preferably selected from the range of preferably about 1 nm to 30 $\mu$m, more preferably about 1 nm to 20 $\mu$m, and still more preferably about 1 nm to about 10 $\mu$m.

The resulting apatite-coated solid composition can be directly used or used as a material for the manufacture of various dosage forms. Parenteral dosage forms can be administered topically (e.g. as intramuscular, subcutaneous, intraorgan, or intraarticular injections, implants, etc.). Moreover, it can be injected into a bone graft substitute or pasted on such a substitute with an adhesive and implanted. Furthermore, products containing the solid composition of the invention may contain more than one species of medicinal substances in combination.

For example, the apatite-coated solid composition can be processed into an injectable product as follows. A clinically useful injection can be produced by suspending the composition together with a dispersant (e.g. a surfactant such as Tween 80, HCO-60, etc., a polysaccharide such as carboxymethylcellulose, sodium alginate, hyaluronic acid, etc., polysorbate, etc.), a preservative (e.g. methylparaben, propylparaben, etc.), an isotonizing agent (e.g. sodium chloride, mannitol, sorbitol, glucose, etc.), a buffer (e.g. calcium carbonate etc.), a pH control agent (e.g. sodium phosphate, potassium phosphate, etc.), and so on. An oily suspension useful as an injection can also be produced by dispersing the composition in a vegetable oil such as sesame oil, corn oil, etc., a mixture of a vegetable oil and a phospholipid such as lecithin, or a medium-chain fatty acid triglyceride (e.g. Miglyol 812).

The particle diameter of the apatite-coated medicinal substance-containing solid composition, taking its use as an injectable suspension as an example, may be within the range satisfying the necessary degree of dispersion and the needle passage requirement. The particle diameter is preferably about 0.1 nm to about 10000 $\mu$m, more preferably about 1 nm to about 1000 $\mu$m, still more preferably about 5 nm to about 500 $\mu$m.

For use as an osseous implant, the solid composition is used in the form of particles about 0.1 to 600 $\mu$m in diameter or may be molded into a block or sheet complementary to the bone defect.

The apatite-coated solid composition can be provided as sterile products by various methods, for example by carrying out the whole production process under clean-room conditions, sterilization with gamma radiation, and addition of an antiseptic, to name but a few typical methods.

The apatite coated solid composition of the present invention can be used to prevent or treat bone diseases (e.g., bone fractures, refracture, osteoporosis, osteomalacia, Behcet's syndrome of bone, ankylosing spondylitis, rheumatoid arthritis, and joint tissue destruction caused by deformation gonarthritis and the related diseases), to repair bone tissue after surgery for multiple myeloma, lung cancer, breast cancer, etc., and to regenerate periodontal tissue in periodontopathy, because it shows a sustained release property with the enhanced activity to bones, and has a sustained-release time for 1 week to 3 months, depending on biodegradable polymer type and content, etc. The pharmaceutical composition of the present invention is particularly effective in bone fracture patients, because the patients are usually fixed the affected portion and covered with plaster bandage and desire to promote the healing by a single administration rather than by multiple administrations. The sustained-release preparation comprising the pharmaceutical composition of the present invention can be used in combination with other active agents. For example, in the case of the compound represented by the formula (I) as osteogenetic promoting substance, as the active agent it can be combined with, mention is made of a formulation of calcium compound (e.g. sodium carbonate), calcitonin, vitamin D (e.g. alfacalcidol), sex hormone (e.g. estrogen, estradiol), prostaglandin $A_1$, bisphosphonic acid, ipriflavone, fluoride compound (e.g. sodium fluoride), vitamin $K_2$, BMP (bone morphogenetic protein), FGF (fibroblast growth factor), PDGF (platelet derived growth factor), TGF-β (transforming growth factor-β), IGF-1 (insulin like growth factor-1), IGF-2 (insulin like growth factor-2), PTH (parathyroid hormone), and so on.

Also, the present composition can be concomitantly used with the above anti-inflammotory agents, antibiotics or analgesics, and so on.

The apatite-coated biodegradable polymer-containing solid composition not containing a medicinal substance can be applied as an adhesive to sites of bone fracture or to the interface between a bone substitute and bone.

Because of its low toxicity, the pharmaceutical composition of the present invention can be safely used in mammals (e.g., humans, bovines, horses, pigs, dogs, cats, mice, rats, rabbits).

The pharmaceutical composition of the present invention, i.e. the present apatite-coated solid composition which also contains a medicinal substance, is expected to serve as a safe preparation of high efficacy proving a constant and long term drug effect with low toxicity, has an osteoconductive activity, and to meet the requirements of the prevention and treatment of bone diseases, repair of damaged bone tissue, and regeneration of periodontal tissue in periodontitis etc., because it releases the drug constantly over an extended period of time. For example, when the pharmaceutical composition of the present invention is used to treat bone fractures (e.g., femoral neck fracture), it can be allowed to efficiently exhibit its osteogenetic promoting action locally and to significantly shorten the healing time, which is conventionally 2 to 6 months following onset of bone fracture. Accordingly, patients shortly return to normal social life, and can be also spared various complication caused by senile bone fractures. The present composition containing an anti-tumor agent exhibits sustained anti-tumor activity to bone tumors, locally. Thus, the present composition containing an anti-tumor agent is an anti-tumor composition with strong activity but is low in toxicity.

The dose of the pharmaceutical composition of the present invention depends on an effective amount of the medicine, although also depending on type and content of the medicine, release time of the medicine, and subject animals, etc. For example, when the pharmaceutical composition of the present invention is used in the form of apatite coated microcapsules to treat a bone fracture portion, it may be administered at about 10 to 500 mg, preferably about 50 to 300 mg, based on the active ingredient content (e.g., compound (I)), once every week to once every 3 months.

When the composition of the present invention is to be used as an adhesive in the repair of bone fractures or a bone graft in the surgical therapy of bone diseases, the dosage is selected according to the required fusion area, generally from the range of about 1 mg to about 100 g per site.

The present apatite-coated solid composition has a property of a prolonged sustained release, and a remarkable osteoconduction. Therefore, the present apatite-coated solid composition can advantageously be used for the prevention or treatment of bone diseases.

The present invention is hereinafter described in more detail by means of the following Reference examples, Examples and Experimental examples, which are not to be construed as being limitative.

Reference Example 1

A 5 g portion of polylactic acid-glycolic acid copolymer (Wako Pure Chemical Industries, Japan, polymerization mole ratio 85:15, weight average molecular weight $1.4 \times 10^4$) was dissolved in 8 ml of methylene chloride. This solution was added to 1600 ml of a 0.1% (w/v) aqueous solution of polyvinyl alcohol (Nippon Gosei Kagaku Kogyo, Japan, Gosenol™ EG-40) followed by intense stirring to prepare an O/W emulsion. After 3 hours of gentle stirring, the emulsion was centrifuged and the pellet was rinsed with water. This pellet was lyophilized to provide microcapsules. The microcapsules were observed with a scanning electron microscope (FIG. 1). At the same time, the microcapsule diameter was measured with a caulter counter. The mean particle diameter was 35 μm.

EXAMPLE 1

Production of Hydroxyapatite-coated Microcapsule Containing a Biodegradable Polymer (1) To a mixture of sodium chloride (16.013 g), sodium hydrogen carbonate (0.706 g), potassium chloride (0.447 g), dipotassium hydrogen phosphate (0.348 g), magnesium chloride hexahydrate (0.610 g), calcium chloride dihydrate (0.735 g), and sodium sulfate (0.142 g) was added sufficient distilled water to make a total of 2 L. This mixture was adjusted to pH 7.4 by adding 0.1 M aqueous solution of hydrochloric acid (11 ml) and 0.1 M aqueous solution of tris(hydroxymethyl)aminomethane (7 ml) to thereby provide an aqueous ion solution.

Figure 2:
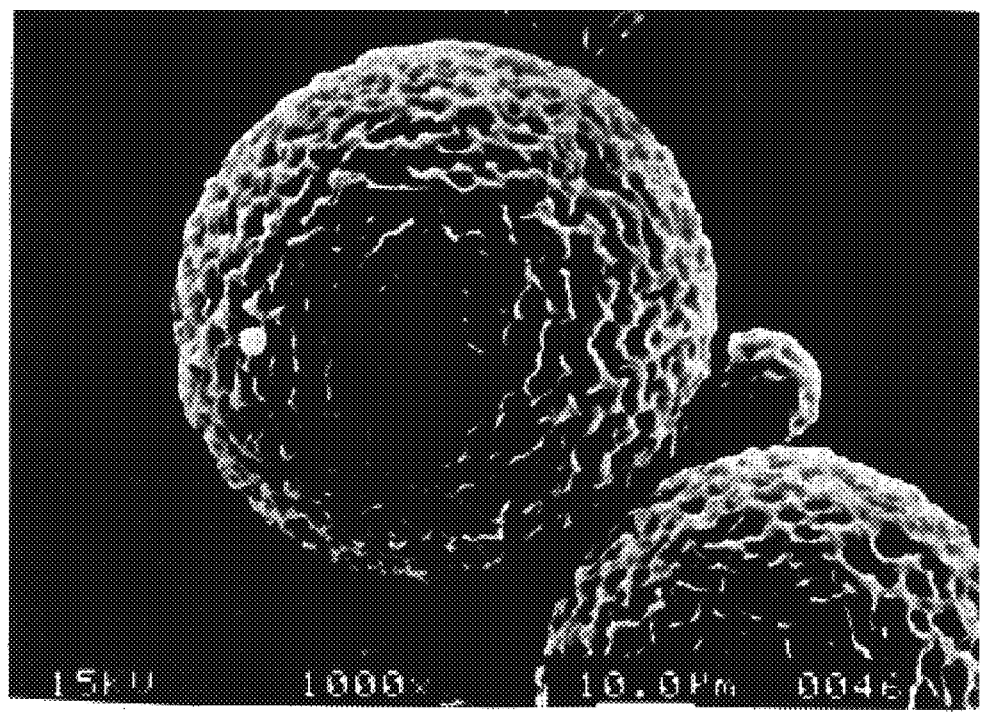
FIG. 2 is a scanning electron microphotograph of the microcapsules obtained in Example 1.

(2) The microcapsules (20 mg) obtained in Reference Example 1 were placed in a vial and 20 ml of the aqueous ion solution prepared under (1) was added. The mixture was stirred well and then allowed to stand in a constant-temperature water bath at 36° C. for 5 days. The mixture was then centrifuged and the resultant hydroxyapatite-coated microcapsules were recovered. Thus obtained microcapsules were examined with a scanning electron microscope (FIG. 2). The mean particle diameter determined with a caulter counter was 39 μm. The surface of microcapsules had been coated with a 2 μm-thick apatite layer of the honeycomb structure.

Reference Example 2

(2R,4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide (hereinafter referred to as compound A) (0.55 g) and lactic acid-glycolic acid copolymer (lactic acid/glycolic acid=85/15 mole %, viscosity 0.164, weight average molecular weight about 14900, Wako Pure Chemical Industries) (4.45 g) were dissolved in dichloromethane (8 ml). This solution was poured into 1600 ml of 0.1% (w/v) aqueous solution of polyvinyl alcohol (Nippon Gosei Kagaku Kogyo, Gosenol™ EG-40) under constant agitation in a turbine homomixer to provide an O/W emulsion.

This O/W emulsion was stirred at room temperature for 3 hours to evaporate off the dichloromethane and the residue was centrifuged. The pellet was redispersed in distilled water and recentrifuged to wash off the free compound A and polyvinyl alcohol The harvested microcapsules were suspended in a small amount of distilled water and the suspension was lyophilized to give microcapsules containing lactic acid-glycolic acid copolymer. The mean particle diameter was 35 μm.

EXAMPLE 2

Production of Apatite-coated Microcapsule Containing Lactic Acid-glycolic Acid Copolymer The microcapsules (20 mg) obtained in Reference Example 2 were placed in a vial and the aqueous ion solution (20 ml) prepared by the manner of Example 1 (1) was added. The mixture was stirred well and then allowed to stand in a constant-temperature water bath at 36° C. for 1 day. The mixture was centrifuged and the pellets were recovered and suspended in 20 ml of fresh aqueous ion solution. The suspension was allowed to stand for a further 4 days at 36° C. This suspension was centrifuged and the pellets were dispersed in distilled water and recentrifuged to wash off the residual aqueous ion solution. The resultant microcapsules were harvested and suspended in a small amount of distilled water and lyophilized to give the desired product. The mean particle diameter determined with a caulter counter was 39 µm. The surface of microcapsules had been coated with a 2 µm-thick apatite layer of a honeycomb structure.

Reference Example 3

The Compound A (0.4 g) and lactic acid-glycolic acid copolymer (lactic acid/glycolic acid=75/25 mole %, viscosity 0.160, weight average molecular weight about 13900, Wako Pure Chemical Industries) (3.6 g) were dissolved in dichloromethane (6.5 ml). This solution was poured into 800 ml of 0.1% (w/v) aqueous solution of polyvinyl alcohol (Nippon Gosei Kagaku Kogyo, Gosenol™ EG-40) under constant agitation in a turbine homomixer to provide an O/W emulsion.

This O/W emulsion was stirred at room temperature for 3 hours to evaporate off the dichloromethane and the residue was centrifuged. The pellet was redispersed in distilled water and recentrifuged to wash off the free compound A and polyvinyl alcohol The harvested microcapsules were suspended in a small amount of distilled water and the suspension was lyophilized to give microcapsules containing lactic acid-glycolic acid copolymer. The mean particle diameter was 38 µm.

EXAMPLE 3
Production of Hydroxyapatite-coated Microcapsule Containing Lactic Acid-glycolic Acid Copolymer and Compound A The microcapsules (50 mg) obtained in Reference Example 3 were placed in a vial and the aqueous ion solution (50 ml) prepared by the manner of Example 1 (1) was added. The mixture was stirred well and then allowed to stand in a constant-temperature water bath at 37° C. for 5 days. The hydroxyapatite-coated and Compound A-containing microcapsules were harvested by filtration.

The residual aqueous ion solution was removed from thus obtained product by washing with distilled water, the product was air blown dried under ultraviolet ray irradiation overnight, and vacuum-dried (40° C.) for one day to give the desired product. The mean particle diameter determined with a caulter counter was 41 µm. The surface of microcapsules had been coated with a 1.5 µm-thick apatite layer of a honeycomb structure.

EXAMPLE 4
Production of Hydroxyapatite-coated Microcapsule Containing Lactic Acid-glycolic Acid Copolymer and Gentamicin In a similar manner as in Reference Example 3 and Example 3 described above employing gentamicin (50 mg) in lieu of the Compound A, the objective microcapsule is produced.

EXAMPLE 5
Production of Hydroxyapatite-coated Microcapsule Containing Lactic Acid-glycolic Acid Copolymer and Taxol In a similar manner as in Reference Example 3 and Example 3 described above employing taxol (50 mg) in lieu of the Compound A, the objective microcapsule is produced.

EXAMPLE 6
Production of Hydroxyapatite-coated Microcapsule Containing Lactic Acid-glycolic Acid Copolymer and Indomethacin In a similar manner as in Reference Example 3 and Example 3 described above employing indomethacin (50 mg) in lieu of the Compound A, the objective microcapsule is produced.

Experimental Example 1
Evaluation on the Release of the Compound A from the Hydroxyapatite-coated Microcapsules Containing Compound A in vitro For use as the in vitro release test solution, an aqueous mixture (50% (v/v), pH 7.4) of polyethylene glycol (Hoechst, Germany, POLYGLYKOL 400) and isotonic phosphate buffer (Wako Pure Chemical Industries, Japan, Dulbecco's PBS (−)) was prepared.

Figure 3:
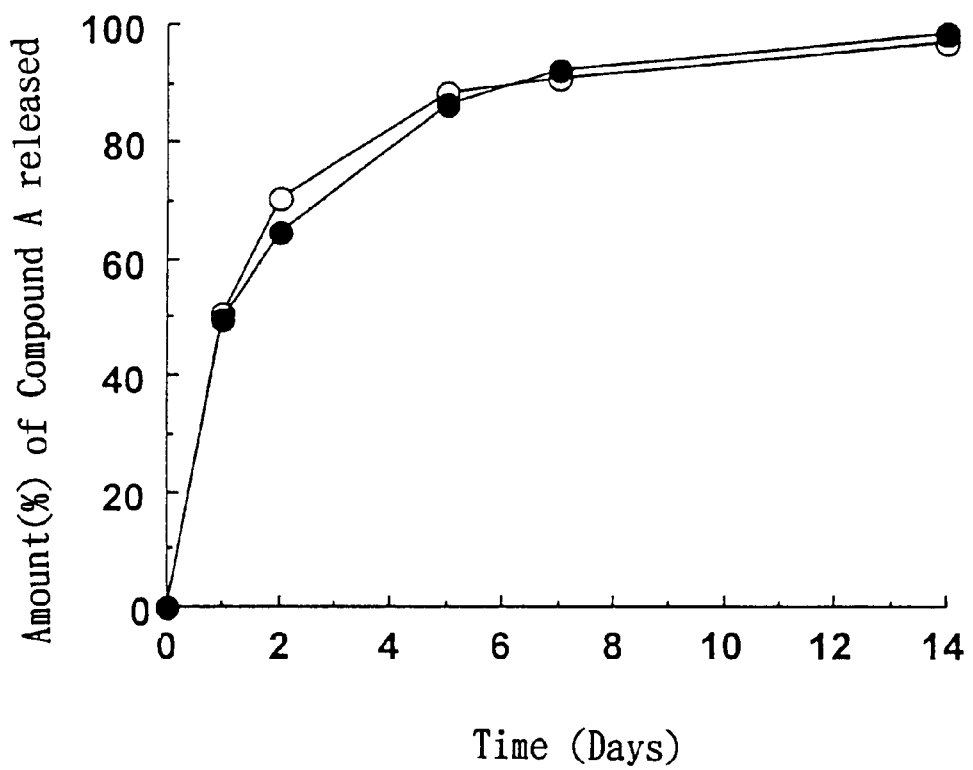
FIG. 3 shows the results of the drug release test in Experimental Example 1.

The apatite-coated microcapsules (ca. 40 mg; containing 3 mg of Compound A) were placed in a vial and 100 ml of the release test solution was added. The mixture was stirred well and preserved in a constant-temperature water bath at 37° C. under shaking (120 strokes/min.). On days 1, 2, 5, 7 and 14, about 500 µl of the test solution was sampled and the amount of release of Compound A was determined by high performance liquid chromatography. As control, the Compound A-contained microcapsules obtained in Reference Example 2 were similarly evaluated. These results are shown in FIG. 3. In the FIG. 3, -●- denotes the results of the hydroxyapatite-coated microcapsule obtained in Example 2, and -○- denotes the results of the control microcapsule obtained in Reference Example 2. As is apparent from FIG. 3, a sustained release of compound A was confirmed from the apatite-coated microcapsules as well and the release kinetics were comparable to the kinetics of the uncoated microcapsules.

Experimental Example 2
The Osteoconductive Activity Evaluated on the Hydroxyapatite-coated Microcapsules in vivo The left legs of a 9 week old SD male rat (n=8) under pentobarbital anesthetization was incised, and the central portion of left fibula was bared and amputated by a cutter.

The hydroxyapatite-coated microcapsules (ca. 50 mg) obtained in Example 1 were filled in the amputated portion of the fibula and the leg was sewn up with stitches.

After 2 weeks, the rat was sacrificed, fibula was excised from the rat, and soft x-ray photography was taken. (FIG. 4(3)).

The amount of bone mineral was measured from the weight of the ashes obtained by burning the bone. The amount of bone mineral on the non-treated right fibula was measured in a similar manner.

The value obtained by subtracting the ash amount of the right fibula from the ash amount of the left fibula was obtained as the amount of bone mineral of the pseudo bone. The results are shown in FIG. 5(3) (* p<0.01).

Figure 4:
FIG. 4 shows the soft x-ray photography, obtained in Experimental Example 2.
Figure 4:
Figure 4:

As a control, similar experiments were carried out on the hydroxyapatite-noncoated microcapsules obtained in Reference Example 1. The results are also shown in FIGS. 4(2) and 5(2). The results of non-treated group are shown in FIGS. 4(1) and 5(1).

Figure 5:
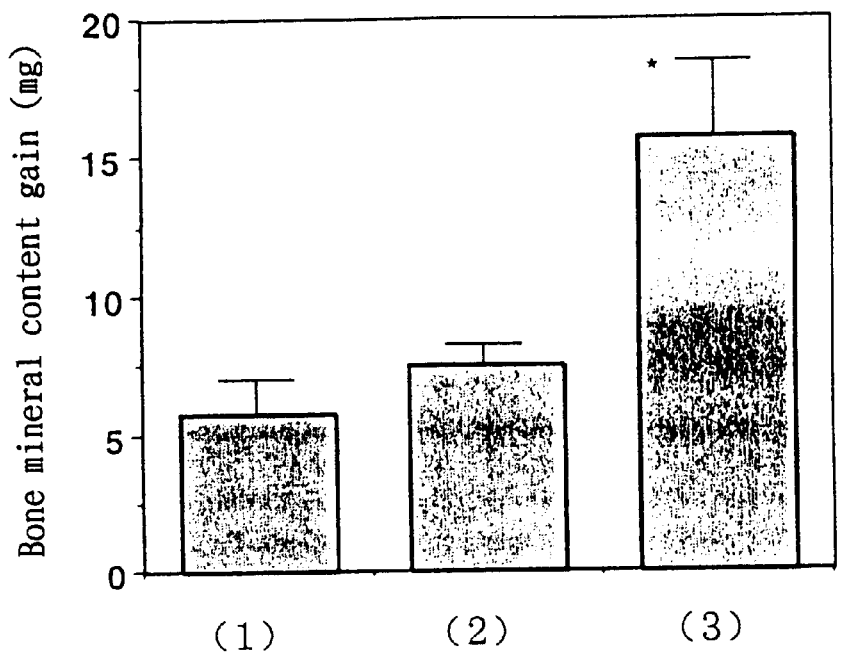
FIG. 5 shows the results of measurements of amounts of bone minerals, obtained in Experimental Example 2.

As is apparent from FIGS. 4 and 5, the administration of hydroxyapatite-coated microcapsules brings about a remarkable increases of pseudo bone area and bone mineral content gain. Thus, the present apatite-coated solid composition has a remarkable osteoconductive property.

Experimental Example 3
The Osteoconductivity Evaluated on the Hydroxyapatite-coated Microcapsules in vivo The left leg of an 11 week old SD male rat (n=6) under diethylether anesthetization was incised, and the central portion of the left fibula was bared and amputated by a cutter and sewn up.

The hydroxyapatite-coated microcapsules (ca. 69 mg; containing 5 mg of Compound A) obtained in Example 3 were dispersed in a solution for dispersion, i.e. an aqueous solution containing 2.5% (w/v) sorbit, 0.9% (w/v) sodium chloride, 0.1% (w/v) polysorbate 80, 0.5% (w/v) carboxymethylcellulose sodium salt and 0.0715% (w/v) disodium phosphate in distilled water, and the dispersion solutions were injected in the amputated portion of the fibula.

After two weeks, the rat was sacrificed, the fibulae were excised, and the amount of bone ash was measured from the weight of the ashes obtained by burning the bone. The amount of bone ash on the non-treated right fibula was measured in a similar manner.

The value obtained by subtracting the ash amount of the right fibula from the ash amount of the left fibula was obtained as the ash weight gain, as the ash amount of bone formation. The results are shown in FIG. 6(2) (* $p<0.01$).

Figure 6:
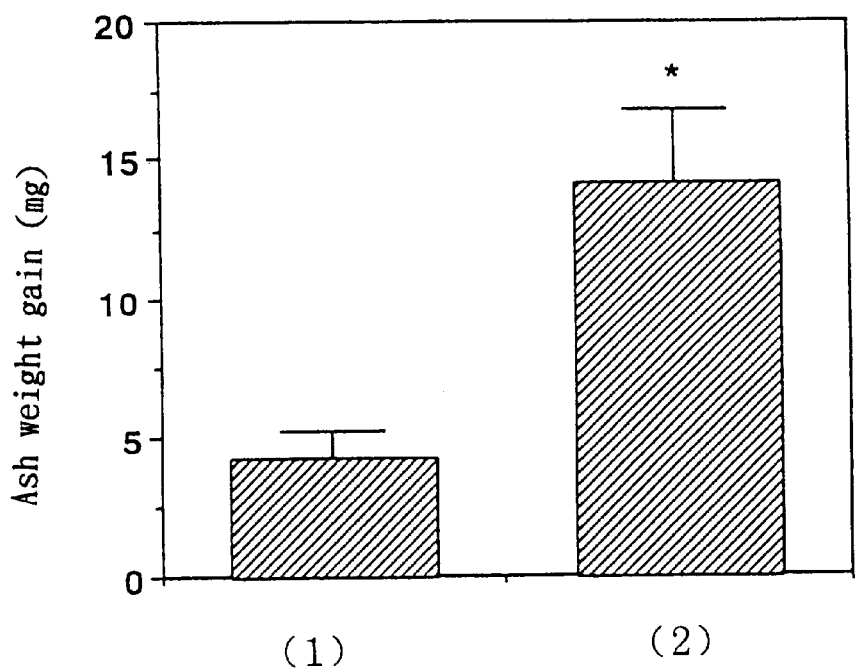
FIG. 6 shows the results of measurement of bone ashes obtained in Experimental Example 3.

As a control, the results of non-treated group are shown in FIG. 6(1).

As is apparent from FIG. 6, the administration of hydroxyapatite-coated microcapsules brings about a remarkable bone weight gain than those of the control group. Thus, the present apatite-coated solid composition has a remarkable bone-formation property.

Industrial Applicability

The apatite-coated biodegradable polymer-containing solid composition not necessarily containing a medicinal substance can be applied as an adhesive to sites of bone fracture or the interface between a bone substitute and bone, in mammals (e.g., humans, bovines, horses, pigs, dogs, cats, mice, rats, rabbits).

The pharmaceutical composition of the present invention, i.e. the present apatite-coated solid composition which also contains a medicinal substance, is expected to serve as a safe preparation of high efficacy proving a constant long term drug effect with low toxicity and meeting the requirements of the prevention and treatment of bone diseases, repair of damaged bone tissue, and regeneration of periodontal tissue in periodontitis etc., because it releases the drug constantly over an extended period of time. For example, when the pharmaceutical composition of the present invention is used to treat bone fractures (e.g., femoral neck fracture), it can be allowed to efficiently exhibit its osteogenetic promoting action locally and to significantly shorten the healing time, which is conventionally 2 to 6 months following onset of bone fracture. Accordingly, patients shortly return to normal social life, and can be also be spared the various complications caused by senile bone fractures. The present composition containing an anti-tumor agent exhibits sustained anti-tumor activity to bone tumors, locally. Thus, the present composition containing an anti-tumor agent is an anti-tumor composition with strong activity but low in toxicity.

The present apatite-coated solid composition has a property of a prolonged sustained release, and a remarkable osteoconductive activity. Therefore, the present apatite-coated solid composition can advantageously be used for the prevention or treatment of bone diseases.

What is claimed is:

1. A solid composition comprising a medicinal substance and an apatite-coated biodegradable polymer selected from the group consisting of polylactic acid, polyglycolic acid, a co-polymer of polylactic acid and polyglycolic acid, or a block polymer selected from polylactic acid, polyglycolic acid and polyethyleneglycol.

2. A solid composition according to claim 1, which comprises a sustained release preparation.

3. A solid composition according to claim 1, wherein the medicinal substance is hardly soluble in water.

4. A solid composition according to claim 1, wherein the medicinal substance is a medicine for treatment of bone diseases, an antibiotic, an anti-inflammatory agent or an anti-tumor agent.

5. A solid composition according to claim 1, wherein the apatite is a crystalline mineral substance which has (1) at least one cation selected from the group consisting of $Na^+$, $K^+$, $H^+$, $Ca^{2+}$, $Sr^{2+}$, $Ba^{2+}$, $Pb^{2+}$, $Zn^{2+}$, $Cd^{2+}$, $Mg^{2+}$, $Fe^{2+}$, $Mn^{2+}$, $Ra^{2+}$, $Al^{3+}$, $Y^{3+}$, $Ce^{3+}$, $Nd^{3+}$, $La^{3+}$ and $Dy^{3+}$, and (2) at least one anion selected from the group consisting of $SO_4^{2-}$, $CO_3^{2-}$, $HPO_4^{2-}$, $PO_3F^{2-}$, $PO_4^{3-}$, $AsO_4^{3-}$, $VO_4^{3-}$, $BO_3^{3-}$, $CrO_4^{3-}$, $SiO_4^{3-}$, $GeO_4^{3-}$, $(CO_3F)^{3-}$ and $BO_4^{5-}$.

6. A solid composition according to claim 1, wherein the apatite is hydroxyapatite.

7. A solid composition according to claim 1, wherein the apatite is phosphate apatite.

8. A solid composition according to claim 1, which is a microcapsule preparation.

9. A solid composition according to claim 1, wherein the apatite layer has a honeycomb structure.

10. A solid composition according to claim 1, wherein the apatite layer is about 1 nm to 50 μm.

11. The composition of claim 1 which is an injectable composition.

12. The composition of claim 1 wherein the polymer composition is a microcapsule preparation.

13. A method for producing an apatite-coated solid composition comprising a medicinal substance and a biodegradable polymer, which method comprises subjecting a substrate of a solid composition comprising a medicinal substance and a biodegradable polymer to immersion in an aqueous ion solution which is capable of forming an apatite.

14. A method according to claim 13, wherein the aquous ion solution is an aqueous solution which comprises at least one of $Na^+$, $K^+$, $Mg^+$, $Ca^+$, $Cl^-$, $CO_3^{2-}$; $PO_4^{3-}$ or $SO_4^{2-}$.

15. A method according to claim 13, wherein the temperature at the immersion is about 10 to 150° C.

* * * * *